United States Patent [19]

Argentino

[11] Patent Number: 5,713,373
[45] Date of Patent: Feb. 3, 1998

[54] RESTRAINT GARMENT

[76] Inventor: Giovanni Argentino, 5025 Wellington, Verdun, Quebec, Canada, H4G 1Y1

[21] Appl. No.: 782,819

[22] Filed: Jan. 13, 1997

[51] Int. Cl.⁶ ........................................... A61B 19/00
[52] U.S. Cl. ........................ 128/869; 128/873; 2/2
[58] Field of Search ....................... 128/845, 846, 128/869, 873, 874, 875, 876; 2/2, 44

[56] References Cited

U.S. PATENT DOCUMENTS

| | | | |
|---|---|---|---|
| 2,230,492 | 2/1941 | Hilby | 128/873 |
| 2,429,168 | 10/1947 | Padgett | 128/873 |
| 2,524,429 | 10/1950 | Devin | 128/873 |
| 3,093,132 | 6/1963 | Bailey | 128/873 |
| 4,206,512 | 6/1980 | Osborne | 128/873 |
| 4,524,768 | 6/1985 | Serrao | 128/873 |
| 4,685,454 | 8/1987 | Posey | 128/873 |
| 4,853,996 | 8/1989 | Harrigan | 128/873 |
| 5,267,352 | 12/1993 | Rodarmel | 128/873 |

*Primary Examiner*—Michael A. Brown
*Attorney, Agent, or Firm*—Robic

[57] ABSTRACT

A restraint garment has a front body portion, permanently connected to a rear body portion, both extending from the neck of the patient down to the mid-height of the patient's thighs. The rear body portion has two detachable pieces connected to each other by a zip fastener. The garment also has first and second rear shoulder portions extending from the shoulder edges of the front body portion down to the bottom of the shoulder blades in the back of the patient, which are detachably connected to each other by another zip fastener. The bottom parts of the front and rear portions are detachably connected to each other by a third zip fastener extending continuously form one thigh to the other, thereby making it possible to completely open the garment at the patient's fork. Each of the zip fasteners are preferably locked either with a key-operated lock or with a buckle made of a snap fastener and a sliding sleeve. This restraint garment makes it difficult not to say impossible for a patient to undress. It is very difficult to remove and prevent the patient from having access to the covered part of his or her body. Moreover, this garment is easy to fit on a patient and gives easy access for the nursing staff to the diaper that the patient may wear and permits the patient to be secured to his or her bed or chair.

16 Claims, 10 Drawing Sheets

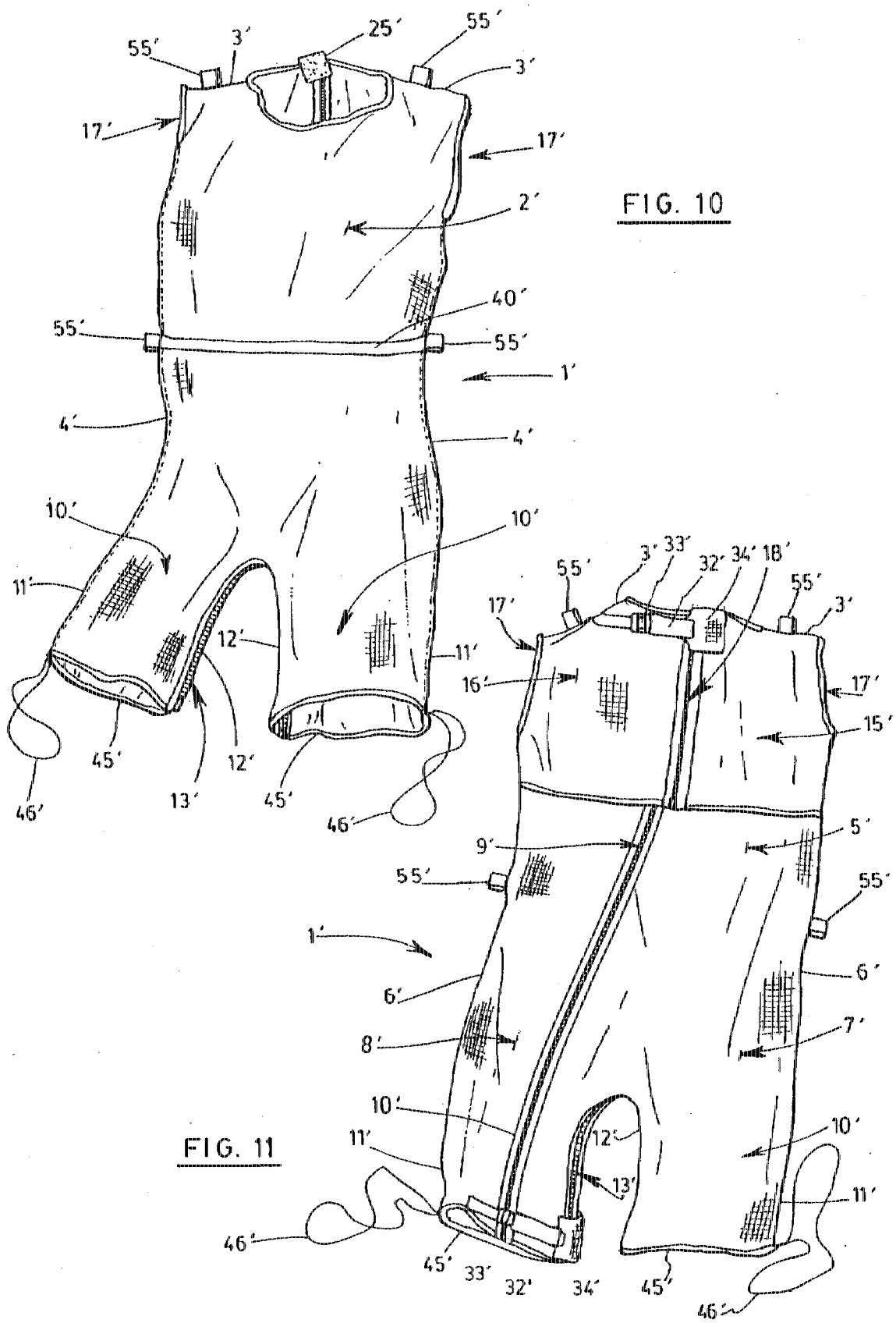

FIG. 17
FIG. 18
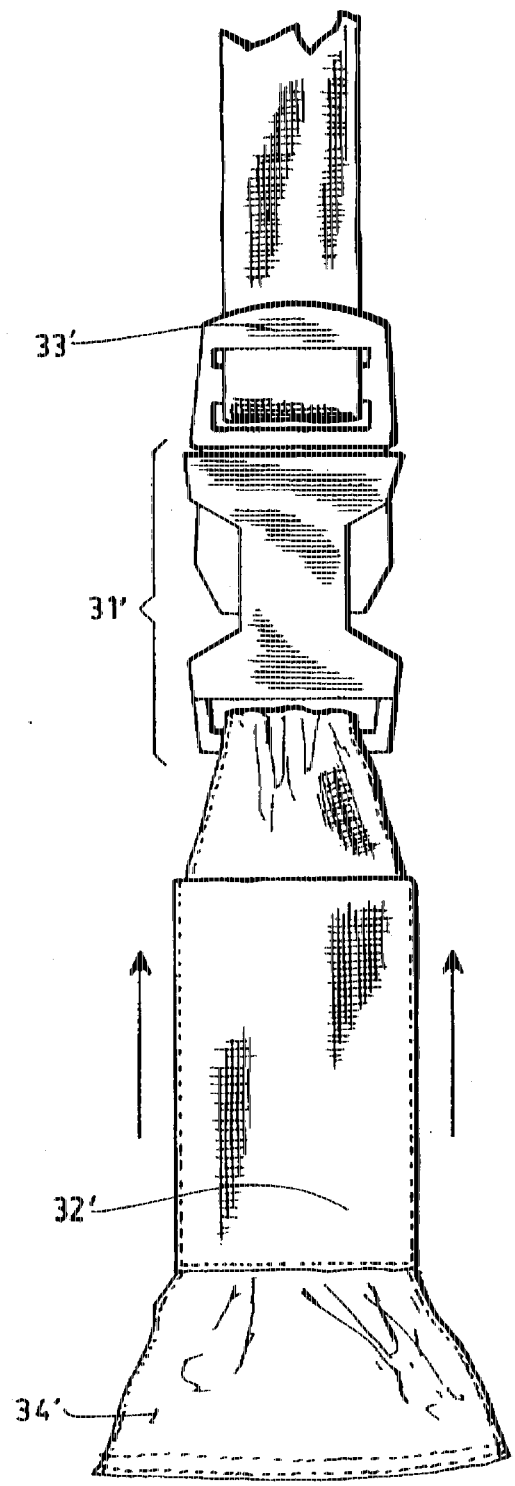
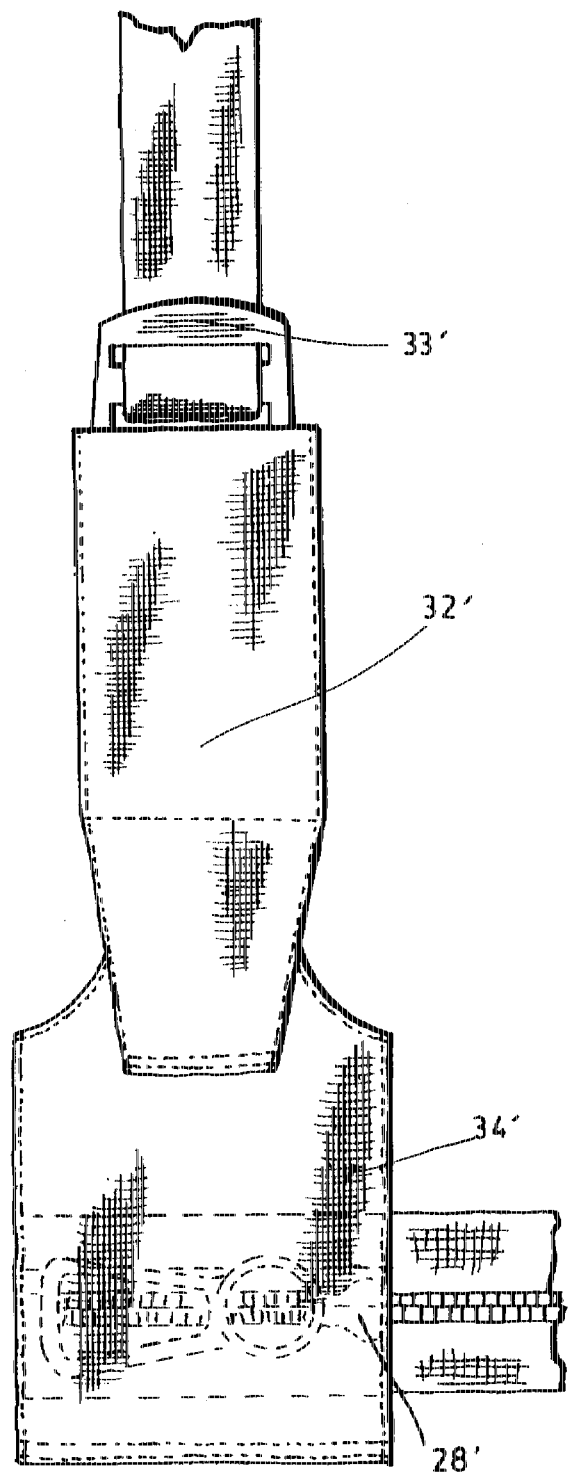

RESTRAINT GARMENT a) Field of the Invention:

The present invention relates to a restrain garment.

b) Brief Description of the Prior Art

It is known that, in hospitals and/or geriatric institutions, some patients, undress themselves because they are senile or are suffering from Alzheimer's syndrome. As a result, the nursing staff is obliged to repeatedly dress them. Therefore, it would be very useful to provide a restraint garment which would prevent its wear from undressing.

It is also known that some patients stretch their skin thereby causing bleeding, because they are suffering from dermatological ailments, such as bedsores. Others are known to scratch themselves compulsively. Therefore, it would also be useful to provide a restraint garment that would prevent the patient wearing it from having access to his or her skin beneath the garment, and thus prevent the patient from aggravating his or her ailment.

It is also known that some patients need to wear diapers. In such a case, the patient's garment should give to the nursing staff an easy access to the diaper but would be devised to prevent the patient from having access for his or her diaper. Thus, it could be useful to provide a restraint garment that would provide easy access for a nursing staff to the diaper, but would prevent the patients from undressing and removing his or her diaper.

It is also known that some patients may be weak, physically disable or impeded by mechanically equipment. Once again, it would be useful to provide a garment which could be easily fitted.

Last of all, it is known that some patients must be secured to their chair or bed, because they are unsettled and would injure themselves by falling down, or leave their room. Once again, it should be useful to have a restraint garment that would permit to the nursing staff to attach the patient to his or her bed or chair.

SUMMARY OF THE INVENTION

The present invention provides a restraint garment which satisfies each of the above mentioned needs.

More particularly, a first object of the invention is to provide a restraint garment which the patient cannot remove.

A second object of the invention is to provide a restraint garment which prevents the patient from having access to his covered body.

A third object of the invention is to provide a restraint garment which permits the patient to be easily diapered.

A fourth object of the invention is to provide a restraint garment which is easy to fit on the patient and to adjust to the patient's size.

A fifth object of the invention is to provide a restraint garment which permits the patient to be secured to his or her bed or chair.

In accordance with the invention, these objects are achieved with a restraint garment comprising a front body portion extending from the neck of the patient down to the mid-height of the patient's thighs. This front body portion has shoulder edges and two side edges.

The restraint garment also comprises a rear body portion permanently connected to the side edges of the front body portion. This rear body portion extends from the armpits of the patient down to mid-height of the patient's thighs.

The front and rear portions have bottom parts that together form shorts for receiving the buttocks and thighs of the patient.

The rear body portion is made of two detachable pieces connected to each other by a first closure means extending at an angle from the central portion of the torso down to one of the rear parts of one of the thighs of the patient.

The restraint garment further comprises first and second rear shoulder portions extending from the shoulder edges of the front body portion down to the bottom of the shoulder blades in the back of the patient. Each of these rear shoulder portions is connected to the front body portion on the shoulder edges and the side edges in such a manner as to define an opening into which the arm of patient is inserted.

The first and second rear shoulder portions are detachably connected to each other by a second closure means extending from the neck of the patient down to the bottom of the shoulder blades of the patient.

The adjacent bottom parts of the front and rear portions have outer side edges permanently connected to each other and inner side edges at the level of the fork of the patient's body that are detachably connected to each other by a third closure means extending continuously from one thigh to the other, thereby making it possible to completely open the garment at the patient's fork.

The closure means preferably consist of size fasteners and each of them is preferably provided with locking means to prevent the patient from opening the same.

Preferably also, attachment loops are fixed on the shoulder edges of the front body and on the side edges of said front body portion at the level of the waist of the patient. In use, these loops can be connected to constraining strips in order to secure the patient to his or her bed or chair.

Thus, the invention provides a restraint garment which makes it difficult not to say impossible for a patient to undress. This garment is very difficult to remove and prevents the patient from having access to his or her body. However, this garment is easy to fit on a patient and gives easy access for the nursing staff to the diaper that the patient wears such diaper.

The invention and its advantages will be better understood by reading the following non-restrictive description of two preferred embodiments thereof, made with reference to the accompanying drawings.

BRIEF DESCRIPTION OF THE DRAWINGS

FIGS. 10 to 16 are views similar to those of FIGS. 1 to 7, respectively, showing a restraint garment according to a second embodiment of the invention;

FIG. 17 is a detailed view of the fastener that is incorporated into the restraint garment of FIGS. 10 to 16; and FIG. 18 is a detailed view of the sliding sleeve covering the fastener shown in FIG. 17;

DESCRIPTION OF TWO PREFERRED EMBODIMENTS OF THE INVENTION

Figures 1, 2:
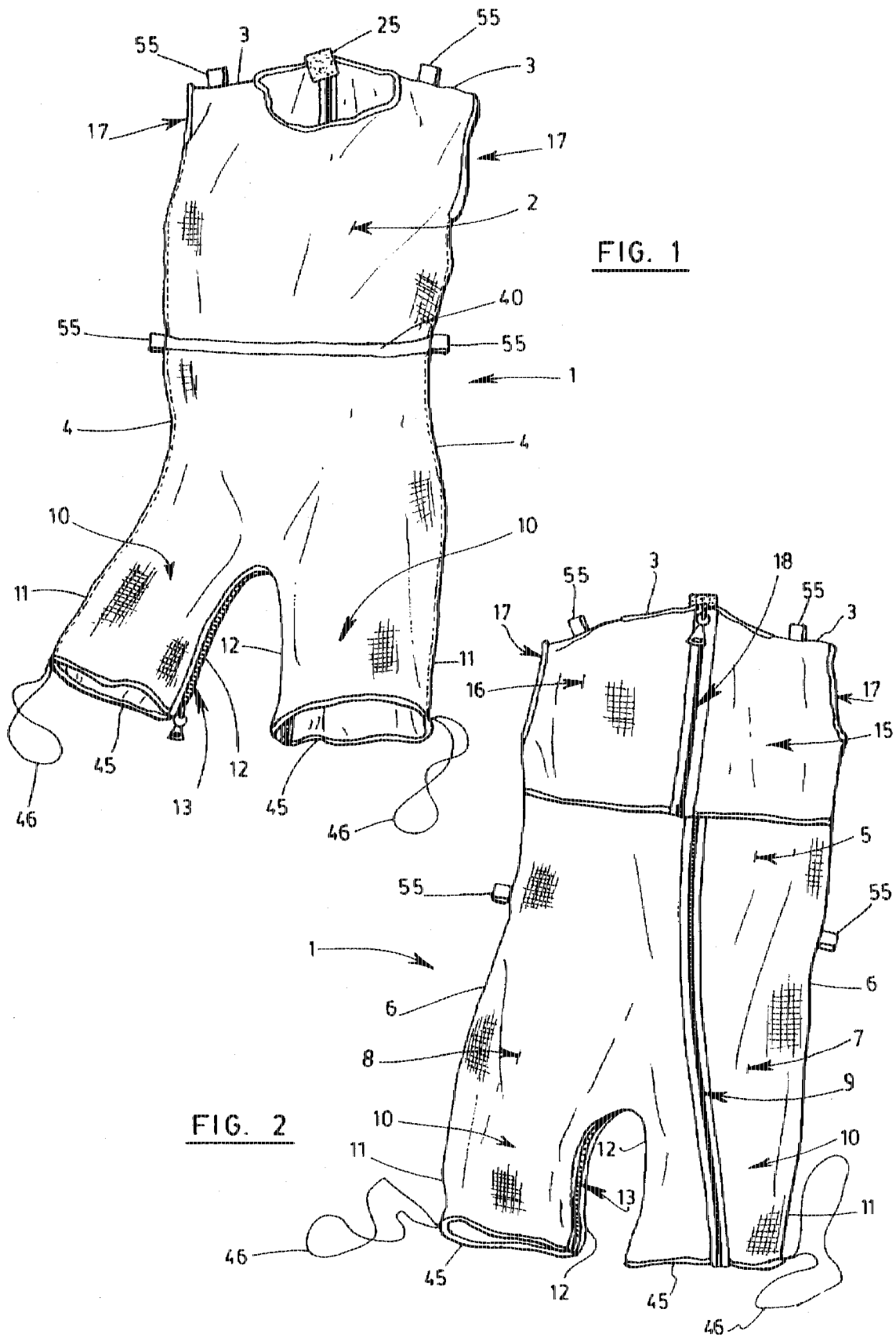
FIG. 1 is a front view of a restraint garment according to a first embodiment of the present invention.
FIG. 2 is a rear view of a restraint garment of FIG. 1.

The restraint garment 1 according to the embodiment of the invention is shown in FIGS. 1 to 7 and 9. As is better shown in FIGS. 1 and 2, this restraint garment 1 comprises a front body portion 2 extending from the neck of the patient down to the mid-height of his or her thighs. The front body portion 2 has two shoulder edges 3 and two opposite side edges 4.

The restraint garment 1 also comprises a rear body portion 5 whose side edges 6 are permanently connected to the side edges 4 of front body portion 2 by means of seams. Instead of such seams, the rear body portion could be made integral to the front body portion. In other words, the front and rear body portions could be made of one single piece.

The rear body portion extends from the armpits of the patient down to mid-height of his or her thighs. As better shown in FIG. 5, the rear body portion 5 is made of two pieces 7 and 8 detachably connected to each other by a closure means 9 extending at angle from the central portion of the torso down to one of the rear part of one of the thighs of the patient. The garment can be totally opened and it is thus easy to dress or undress the patient. However, as the end of the closure means is at the central portion of the torso in the back of the patient, it is hard for the patient to reach for it and open it by him or herself.

As shown in FIGS. 1, 2, 5 to 7, the front 2 and rear 5 portions have two bottom parts 10 that together form shorts for receiving the buttock and thighs of the patient.

As better shown in FIGS. 1 and 2, the bottom parts 10 of front 2 and rear 5 portions have outer side edges 11 permanently connected to each other. They also have inner side edges 12 at the level of the fork of the patient's body. These inner side edges 12 are detachably connected to each other by a closure means 13 extending continuously from one thigh to the other, thereby making it possible to completely open the garment at the patient's fork and thus provides easy access to a diaper.

As shown in FIG. 2, the garment 1 further comprises first and second rear shoulder portions 15 and 16 extending from the two shoulder edges 3 of the front body portion 2 down to the bottom of the shoulder blades in the back of the patient. Each of these rear shoulder portions 15 and 16 is connected by a seam to the front body portion 2 on the shoulder edges 3 and the side edges 6 in such a manner as to define an opening 17 in which the arm of patient can be inserted. However, they could be made integral to the front body portion.

As shown in FIG. 2, the first and second rear shoulder portions 15 and 16 are detachably connected to each other by a closure means 18 extending from the neck of the patient down to the bottom of the shoulder blades of the patient. These rear shoulder portions 15 and 16 cover the upper part of the rear body portion 2 and make it more difficult for the patient to reach the closure means of the rear body portion 2 and to open it.

Figure 3:
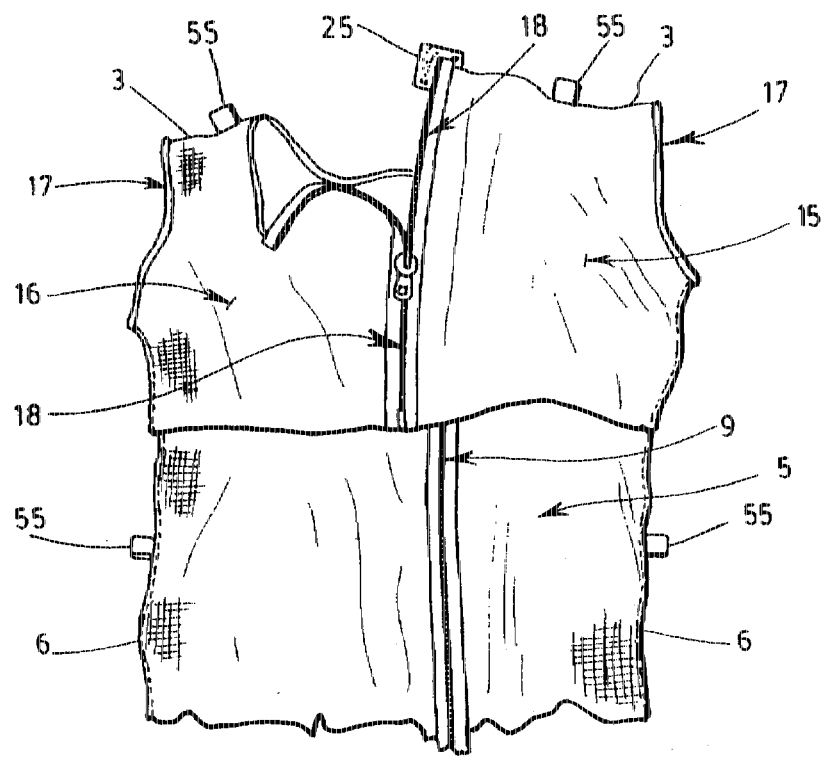
FIG. 3 is a detailed view of the upper portion of the back of the restraint garment of FIG. 1, shown in slightly opened position.
Figure 4:
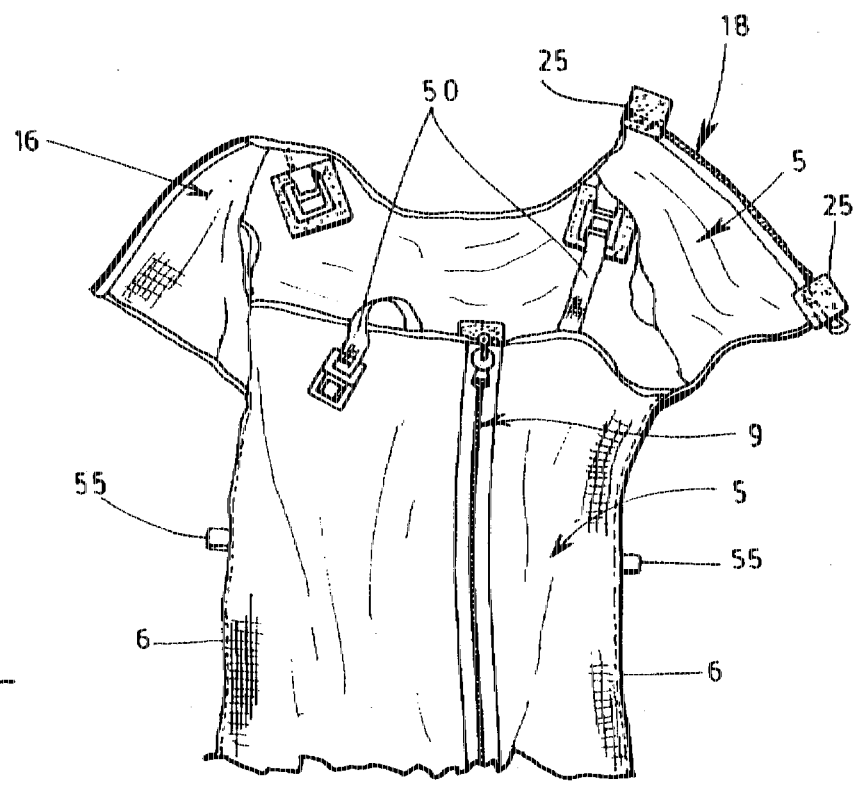
FIG. 4 is a detailed view of the upper portion of the back of the restraint garment of FIG. 1, shown in completely opened position, with one of the shoulder strap opened.
Figure 5:
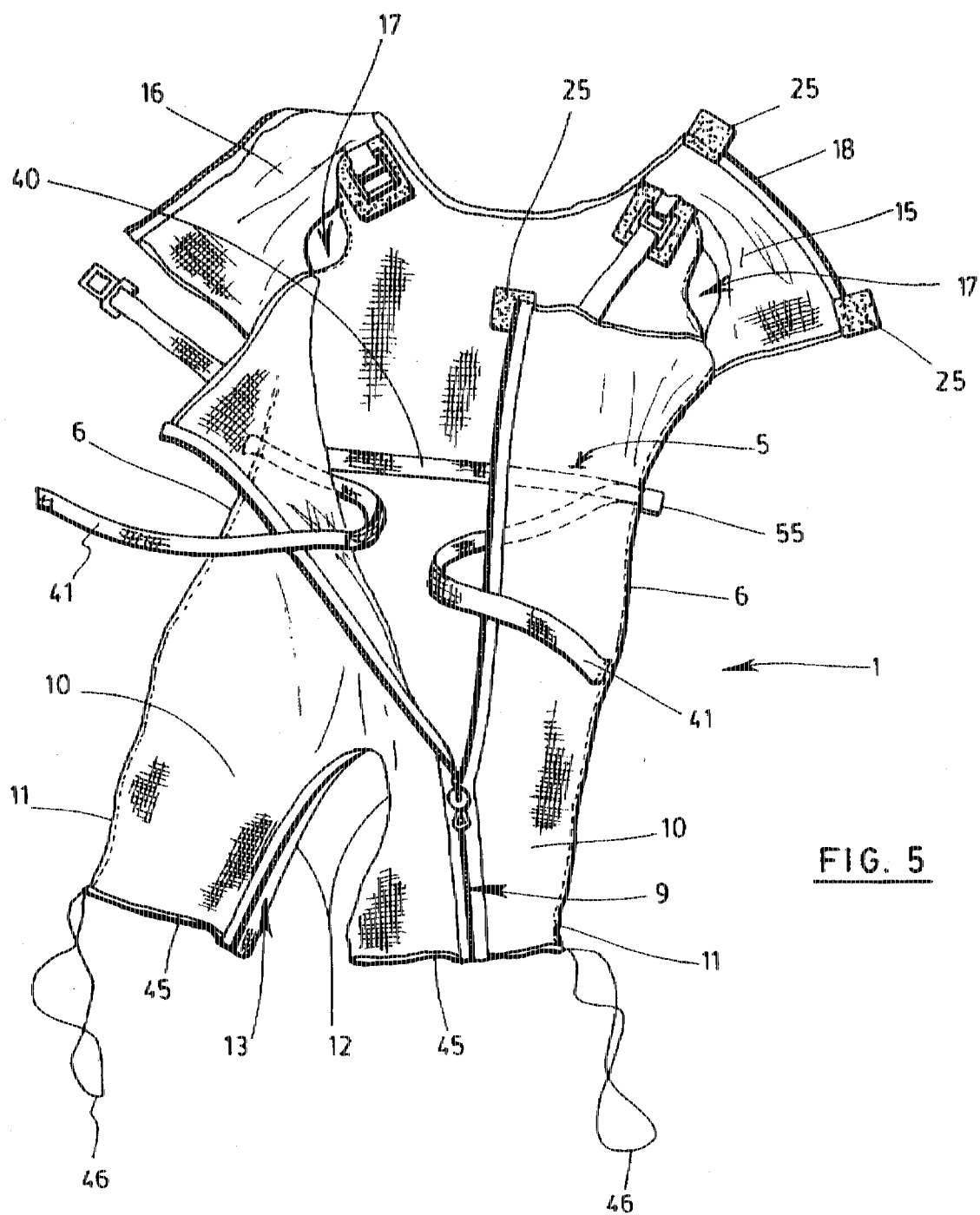
FIG. 5 is a rear view of the restraint garment of FIG. 1, shown in partially opened position.
Figure 6:
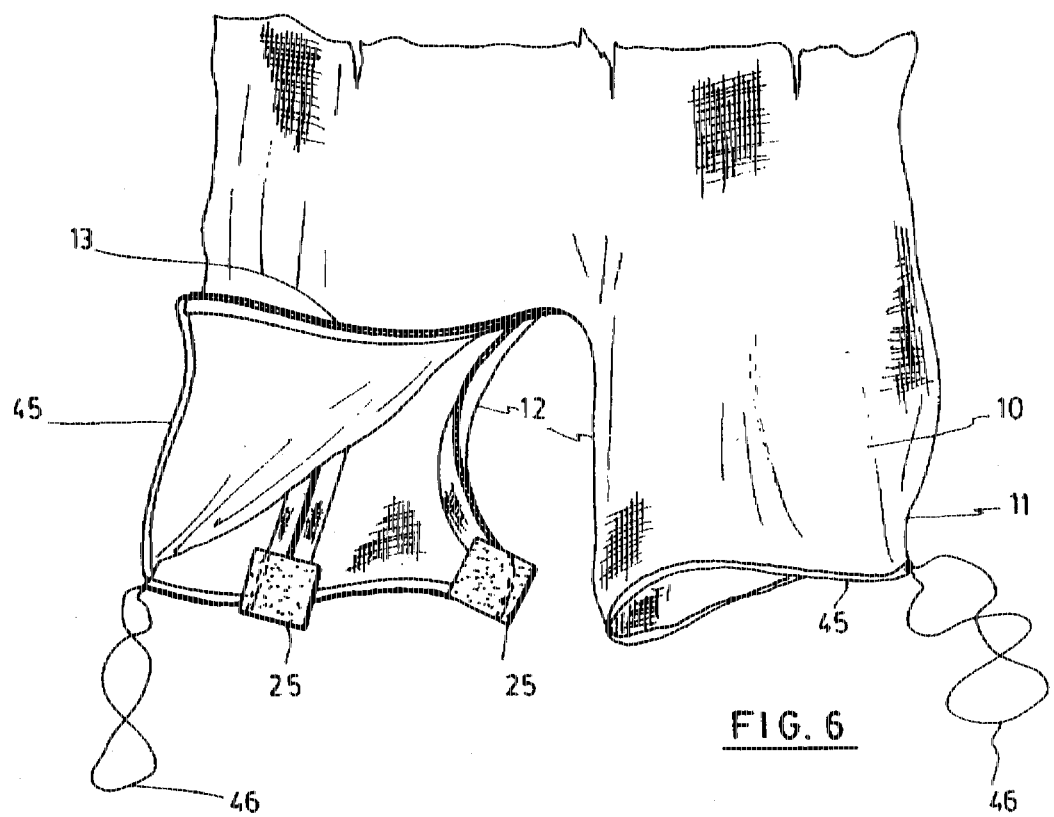
FIG. 6 is a detailed front view of the bottom parts of the restraint garment of FIG. 1, shown in partially opened position.
Figure 7:
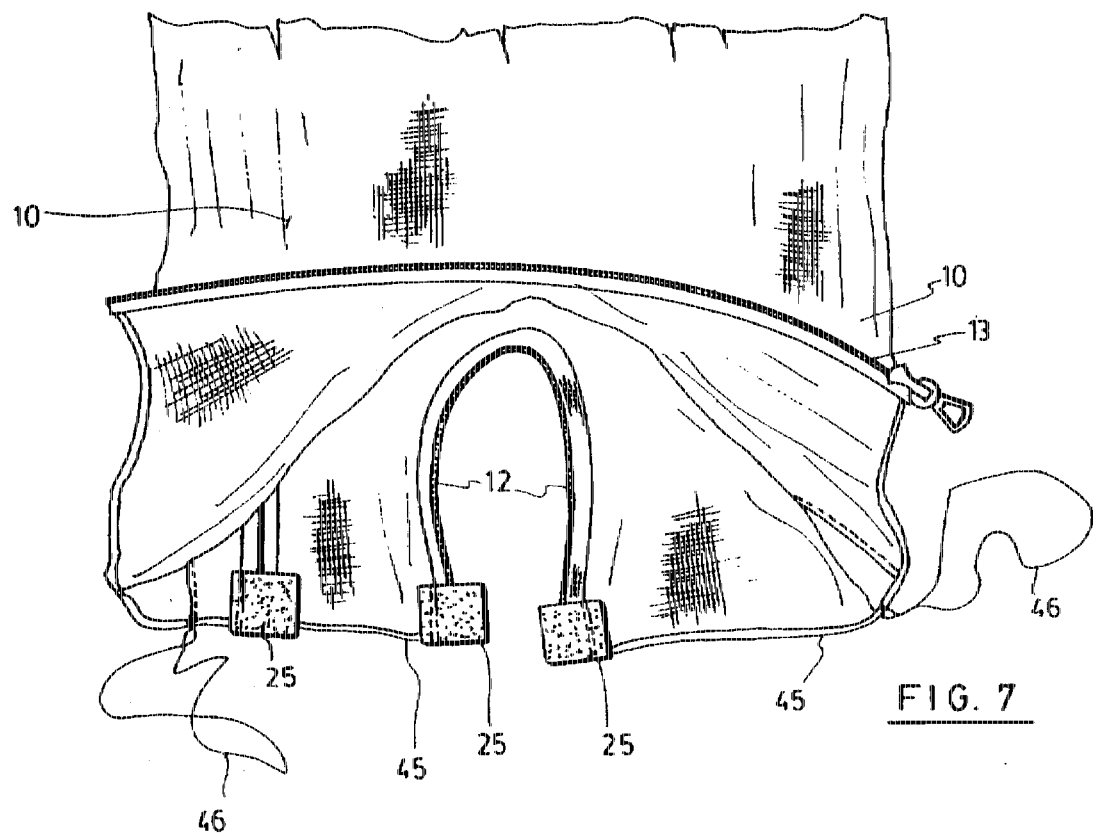
FIG. 7 is a detailed front view of the bottom parts of the restraint garment of FIG. 1, shown in totally opened position.

As shown in FIGS. 1 to 7 and 9, all the closure means of the garment are preferably zip fasteners. Each zip fastener has a pair of opposite ends with opposite sides. A pad 25 is fixed on one of the opposite end of each zip fastener so as to protect the patient from chafing by contact with the adjacent corresponding portion zip fastener. An example is shown in FIG. 4, where the two pads 25 located at each opposite end of the zip fastener 18 of the rear shoulder portion 15.

The zip fasteners can be provided with locking means to prevent the patient from opening the same. Such locking means must be selected to nevertheless allow the garment to be easily and quickly opened by the nursing staff, especially in case of emergency.

Figure 9:
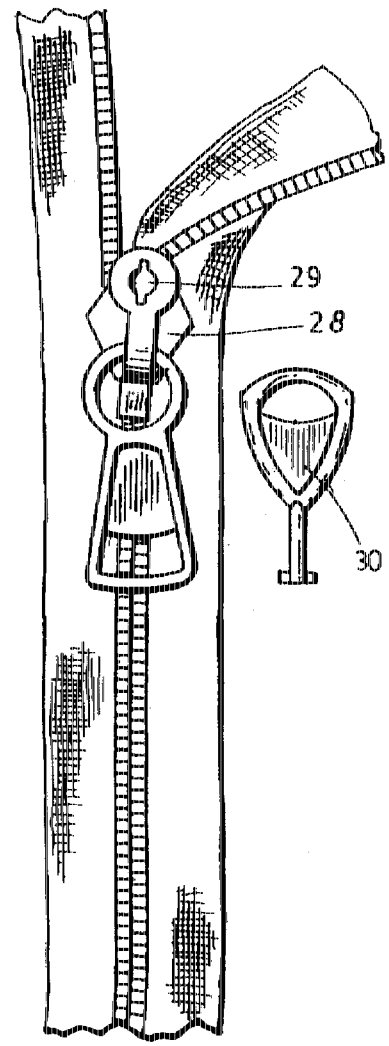
FIG. 9 is a detailed view of the key-operated lock that can be incorporated into the zip fasteners of the restraint garment of FIG. 1.
Figure 12:
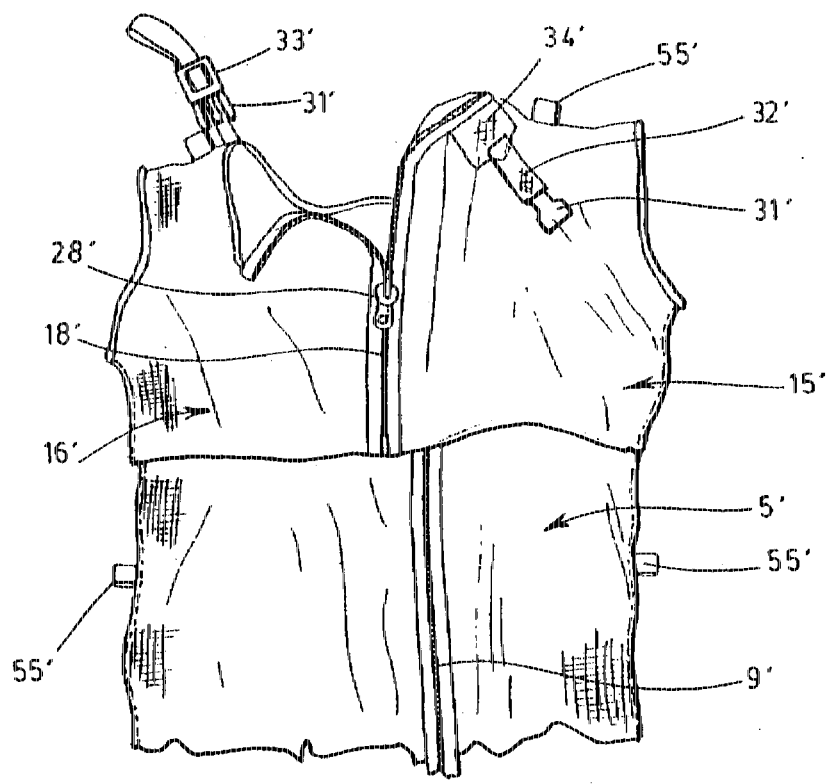
Figure 13:
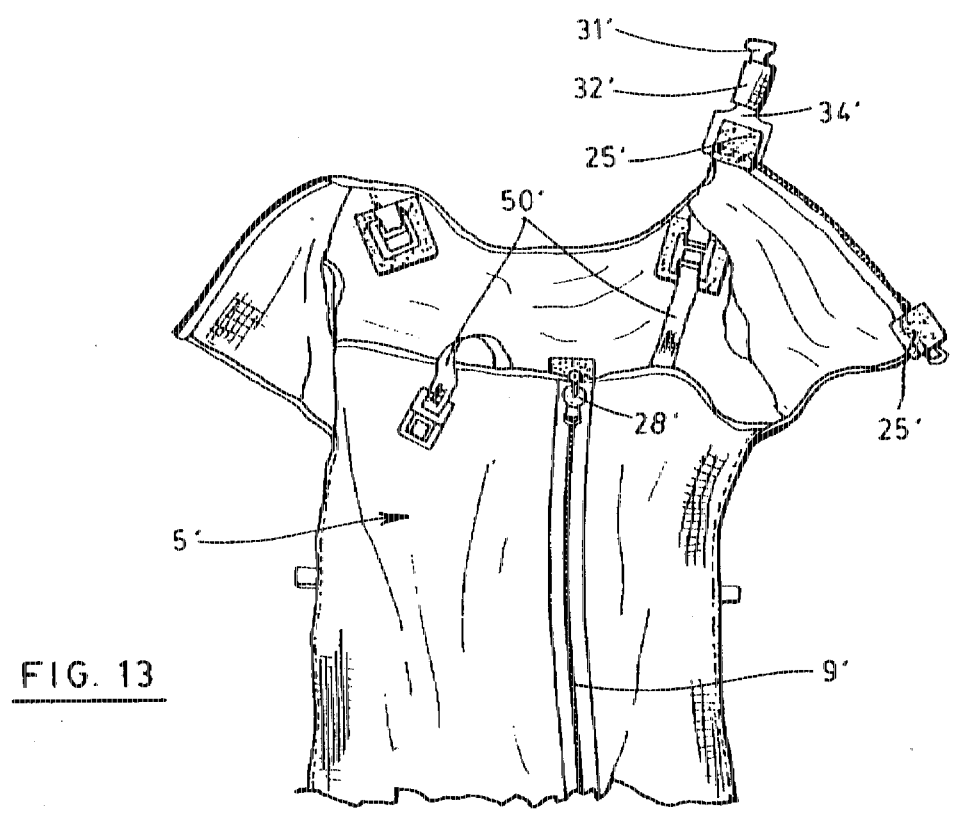
Figure 14:
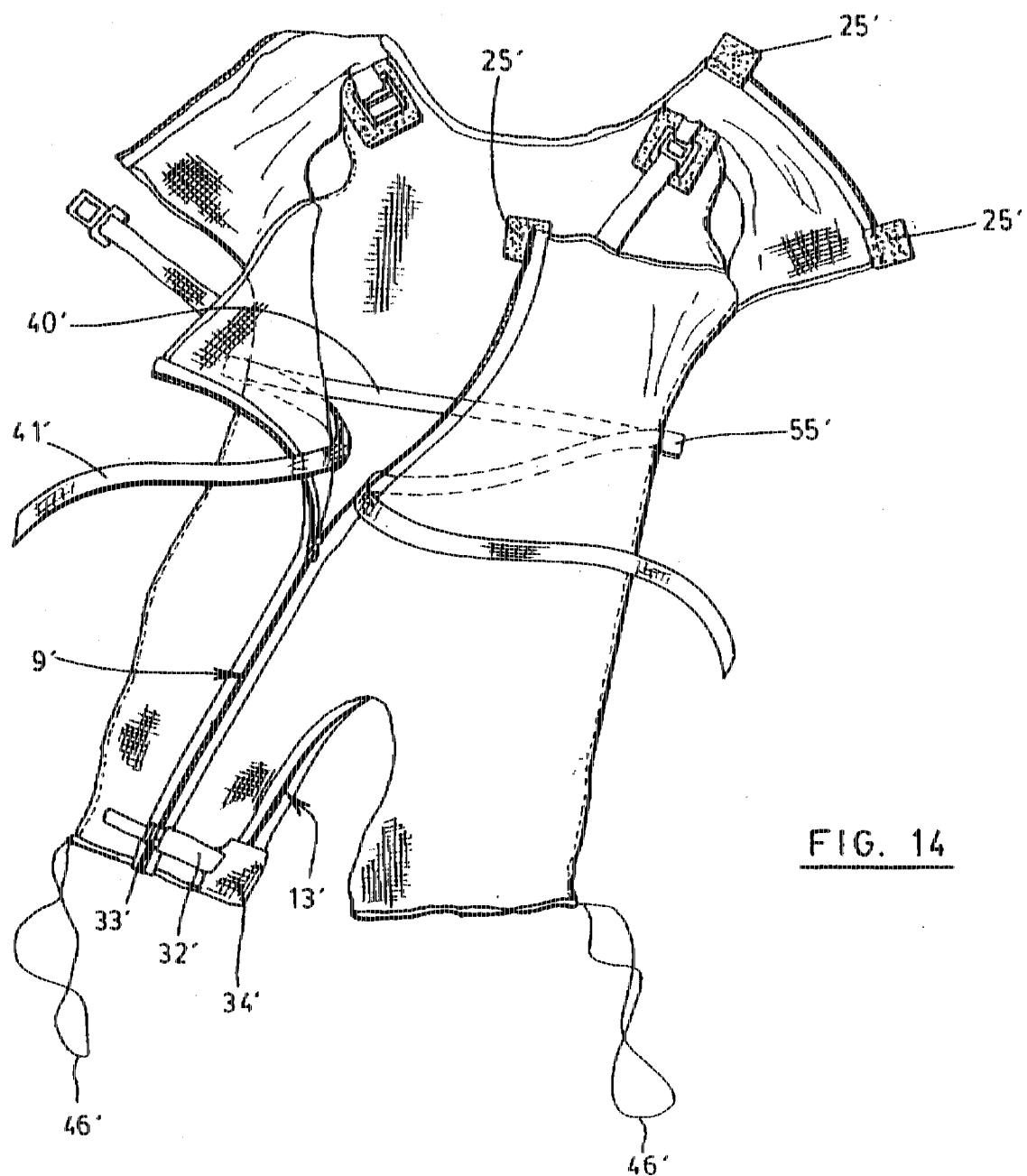
Figure 15:
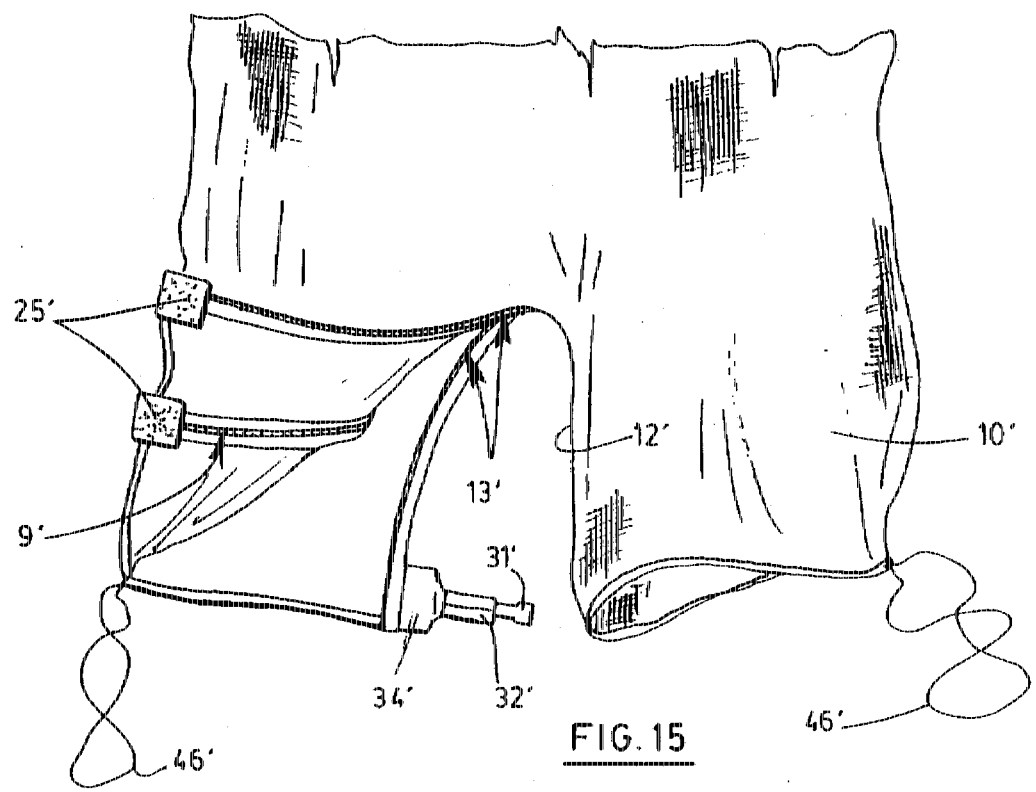
Figure 16:
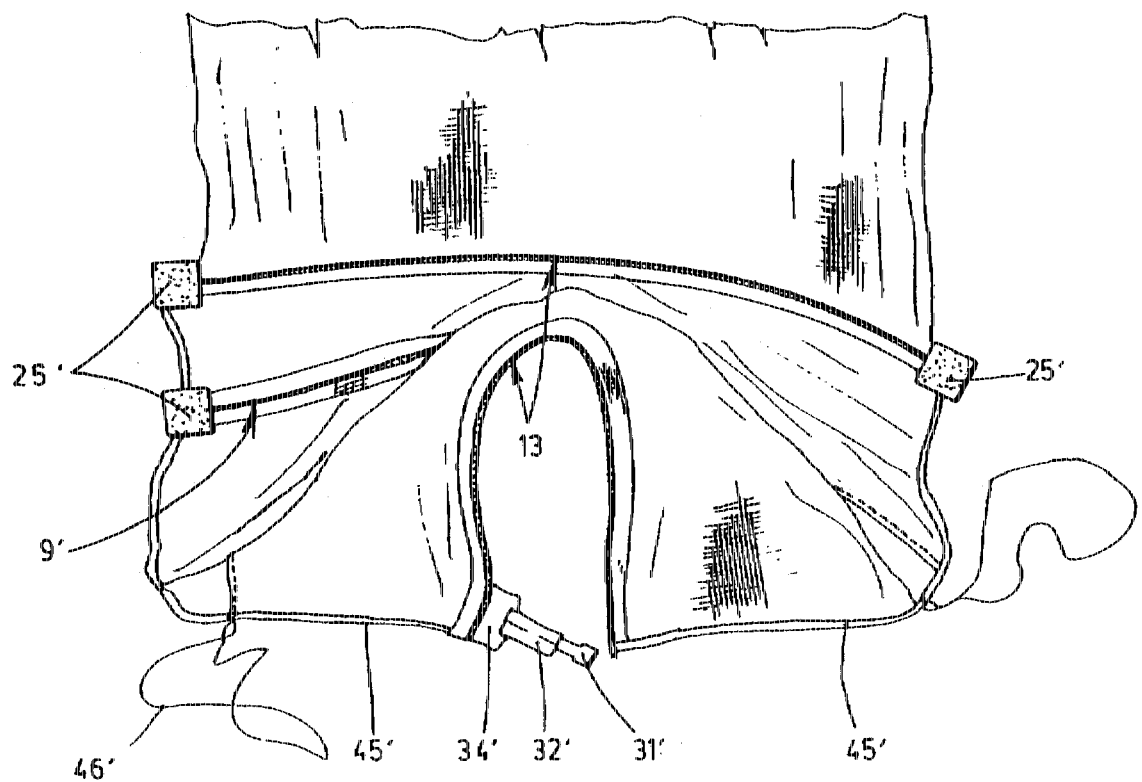

In the first illustrated embodiment shown in FIGS. 1 to 7, the locking means consist of a lock 29 that is incorporated into the movable element 28 of each zip fastener and is operable with a key 30. This feature is illustrated in FIG. 9.

In the second embodiment shown in FIGS. 10 to 16, the closure means consist of a flap 34' that is sewn close to the end of the zip fasteners and can be folded onto this end to cover and hidden the movable element of the zip fastener. This flap 34' can be fixed in this position by means of a buckle made of a snap fastener 31' protected by a sliding sleeve 32". The length of this buckle can be made adjustable at 33'. This feature is shown in FIGS. 10 and 11.

The restraint garment 1 is preferably devised to make it adjustable to the size of the patient. It is also devised to prevent the patient from having access under his or her garment. For this purpose, the front body portion 2 may incorporate a belt 40 at the level of the waist of the patient as shown in FIG. 1. This belt 40 extends within the restraint garment 1 and has a pair of opposite ends 41 (see FIG. 5) that project from both sides of the front body portion. These opposite ends 41 can be tied up together in the back of the patient within the garment.

As shown in FIG. 1, the bottom parts 10 of the front 2 and rear portions 5 which extend down to mid-height of the patient's thighs, may also comprise a hem 45 in which an adjustment cord 46 is freely mounted.

Figure 8:
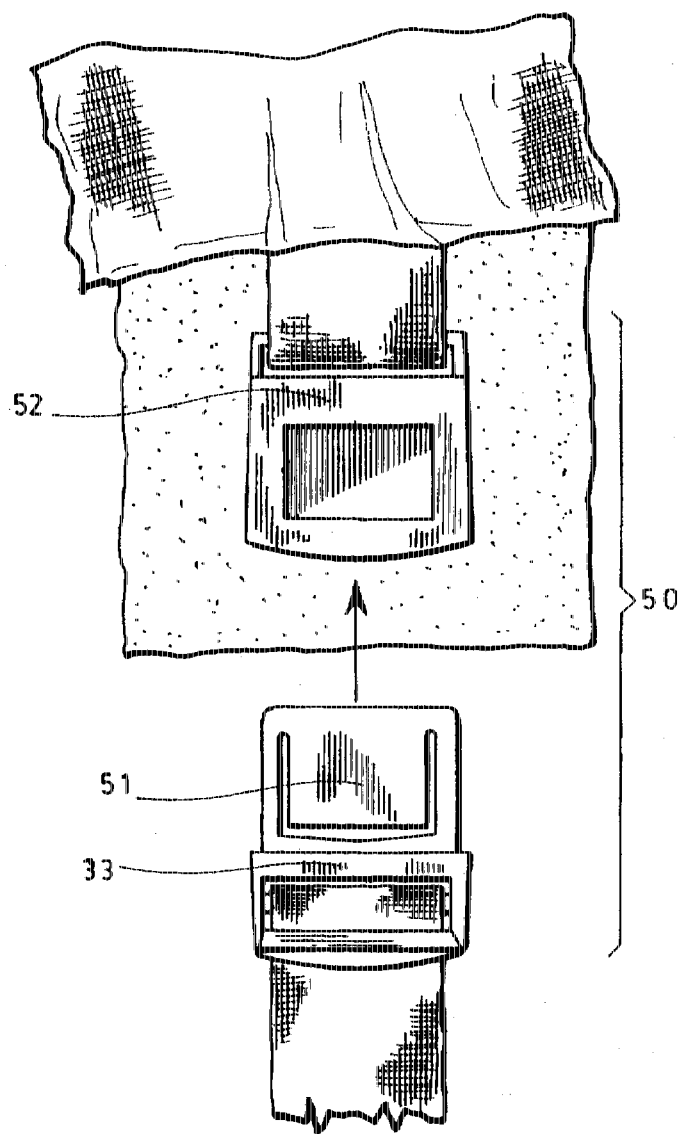
FIG. 8 is a detailed view of the adjustable shoulder strap that can be incorporated in the restraint garment according to the invention whatever be the illustrated embodiment.

As shown in FIG. 4, the upper part of the front body portion 2 may be linked to the upper part of the rear body portion 5 by means of a pair of adjustable shoulder straps 50 whereby the garment can be adjusted in height. A detailed view of the shoulder strap, shown in totally opened position is given in FIG. 8. As is shown, the bottom part 51 fits in the upper part 52. The length of the strap can be adjusted with an adjustable buckle 33.

In order to secure the patient to his or her bed or chair, the garment 1 may further comprise attachment loops 55 fixed on the shoulder edges 3 of the front body 2 and on the side edges 6 of the front body portion 2 at the level of the waist of the patient (see FIG. 3). These loops can be connected to constraining strips (not shown) attached to a chair or bed.

The restraint garment 1' according to the second embodiment of the invention as shown in FIGS. 10 to 18 is similar to the garment 1, except for a few minor differences. For this reason, the same reference numerals as in FIGS. 1 to 7 have been used in FIGS. 10 to 16 to identify the same structural elements, with a distinguishing prime (').

As will be seen, a first difference lies in the angle at which the closure means 9' extends on the rear body portion 5. In this connection, it may be appreciated that such angle is not actually relevant as the closure means 9' may extend down towards any one of the thighs of the patient.

A second difference already mentioned hereinabove lies in the kind of locking means used to prevent the patient from opening the closure means (viz. the zip fasteners 9', 13' and 18'). These locking means shown in FIGS. 17 and 18 consist of flaps 34' that can be folded and locked over the movable elements 28 of the zip fasteners to hidden the same.

Whatever be the illustrated embodiment, the restraint garment according to the invention is preferably made from a soft, yet strong, fabric, which is preferably in the form of a mesh. This fabric is preferably nylon, and keeps the restrained person cool. It is lightweight and can be easily and quickly washed and dried.

Of course, numerous modifications could be made to the above described embodiments without departing the scope of the invention as defined in the appended claims.

I claim:

1. A restraint garment for preventing a patient from undressing, said garment comprising:

a front body portion extending from the neck of the patient down to the mid-height of his or her thighs, said front body portion having shoulder edges and two side edges;

a rear body portion permanently connected to the side edges of said front body portion, said rear body portion extending from the armpits of the patient down to mid-height of his or her thighs, said rear portion being made of two pieces detachably connected to each other by a first closure means extending at angle from the central portion of the torso down to one of the rear part of one of the thighs of the patient;

first and second rear shoulder portions extending from the shoulder edges of the front body portion down to the bottom of the shoulder blades in the back of the patient, each of said rear shoulder portions connected to the front body portion on the shoulder edges and the side edges in such a manner as to define an opening in which the arm of patient can be inserted, said first and second rear shoulder portions being detachably connected to each other by a second closure means extending from the neck of the patient down to the bottom of the shoulder blades of the same;

said front and rear portions having bottom parts that together form shorts for receiving the buttock and thighs of said patient;

the adjacent bottom parts of said front and rear portions having outer side edges permanently connected to each other and inner side edges at the level of the fork of the patient's body that are detachably connected to each other by a third closure means extending continuously from one thigh to the other, thereby making it possible to completely open the garment at the patient's fork.

2. The garment of claim 1, wherein said first, second and third closure means are zip fasteners.

3. The garment of claim 2, wherein at least said first and third closure means are provided with locking means to prevent the patient from opening the same.

4. The garment of claim 3, wherein said locking means consist of key-operated locks incorporated into said zip fasteners.

5. The garment of claim 3, wherein said locking means consist of a buckle made of a snap fastener and protected by a sliding sleeve.

6. A garment as claimed in claim 3, wherein:

each zip fastener has a pair of opposite ends with opposite sides, and wherein a pad is fixed on one of the opposite sides of each opposite end of each zip fastener so as to protect the patient from chafing by contact with the zip fastener;

the front body portion incorporates a belt at the level of the waist of the patient, said belt extending within said garment and having a pair of opposite ends that project from both sides of the front body portion, whereby tying up of said two ends together in the back of the patient, permits to adjust the size of the garment;

the bottom parts of the front and rear portions extend down to mid-height of the patient's thighs and comprise a hem in which an adjustment cord is freely mounted, thereby making it possible to adjust the size of these bottom parts so as to prevent the patient from having access under his or her garment; and the upper part of the front body portion is linked to the upper part of the rear body portion by means of a pair of adjustable shoulder straps, whereby the garment can be adjusted in height.

7. A garment as claimed in claim 6, further comprising attachment loops fixed on the shoulder edges of the front body and on the side edges of said front body portion at the level of the waist of the patient, whereby said loops can be connected to constraining strips in order to secure the patient to his or her bed or chair.

8. The garment of claim 7, wherein said locking means consist of key-operated locks incorporated into said zip fasteners.

9. The garment of claim 7, wherein said locking means consist of a buckle made of a snap fastener and protected by a sliding sleeve.

10. A garment as claimed in claim 7, which is made from a mesh material.

11. A garment as claimed in claim 2, wherein each zip fastener has a pair of opposite ends with opposite sides, and wherein a pad is fixed on one of the opposite sides of each opposite end of each zip fastener so as to protect the patient from chafing by contact with the zip fastener.

12. A garment as claimed in claim 1, wherein the front body portion incorporates a belt at the level of the waist of the patient, said belt extending within said garment and having a pair of opposite ends that project from both sides of the front body portion, whereby tying up of said two ends together in the back of the patient, permits to adjust the size of the garment.

13. A garment as claimed in claim 1, wherein the bottom parts of the front and rear portions extend down to mid-height of the patient's thighs and comprise a hem in which an adjustment cord is freely mounted, thereby making it possible to adjust the size of these bottom parts so as to prevent the patient from having access under his or her garment.

14. A garment as claimed in claim 1, wherein the upper part of the front body portion is linked to the upper part of the rear body portion by means of a pair of adjustable shoulder straps, whereby the garment can be adjusted in height.

15. A garment as claimed in claim 1, further comprising attachment loops fixed on the shoulder edges of the front body and on the side edges of said front body portion at the level of the waist of the patient, whereby said loops can be connected to constraining strips in order to secure the patient to his or her bed or chair.

16. A garment as claimed in claim 1, which is made from a mesh material.

\* \* \* \* \*